US008212065B2

(12) United States Patent
Breit et al.

(10) Patent No.: US 8,212,065 B2
(45) Date of Patent: Jul. 3, 2012

(54) METHOD FOR THE PRODUCTION OF OPTICALLY ACTIVE ALPHA ALKYL CARBONYL COMPOUNDS

(75) Inventors: Bernhard Breit, Gundelfingen (DE); Christopher Studte, Freiburg (DE)

(73) Assignee: Albert-Ludwigs-Universitat Freiburg, Freiburg (DE)

( * ) Notice: Subject to any disclaimer, the term of this patent is extended or adjusted under 35 U.S.C. 154(b) by 350 days.

(21) Appl. No.: 12/679,125

(22) PCT Filed: Sep. 18, 2008

(86) PCT No.: PCT/EP2008/007818
§ 371 (c)(1),
(2), (4) Date: Mar. 19, 2010

(87) PCT Pub. No.: WO2009/040054
PCT Pub. Date: Apr. 2, 2009

(65) Prior Publication Data
US 2010/0305352 A1 Dec. 2, 2010

(30) Foreign Application Priority Data
Sep. 24, 2007 (DE) .......................... 10 2007 045 624

(51) Int. Cl.
*C07C 309/79* (2006.01)
*C07C 69/24* (2006.01)
*C07C 233/01* (2006.01)
(52) U.S. Cl. ........................ 558/54; 560/219; 564/129
(58) Field of Classification Search .................. None
See application file for complete search history.

(56) References Cited

U.S. PATENT DOCUMENTS
4,723,033 A 2/1988 Erickson
2009/0209780 A1 8/2009 Koura et al.

FOREIGN PATENT DOCUMENTS
WO WO 2007/013555 A1 2/2007

OTHER PUBLICATIONS

International Preliminary Report on Patentability, Form PCT/IB/373, for PCT International Patent Application No. PCT/EP2008/007818 corresponding to U.S. Appl. No. 12/679,125, mailing date May 4, 2009.
Oppolzer, Wolfgang, et al., "Camphorsulfonamide-Shielded, Asymmetric 1,4-Additions and Enolate Alkylations; Synthesis of a Southern Corn Rootworm Pheromone. Preliminary Communication". Helvetica Chimica Acta, 1984, vol. 68, No. 1, pp. 212-215. (Abstract).

Evans, D.A., et al., "Enantioselective Aldol Condensations. 2. Erythro-Selective Chiral Aldol Condensations via Boron Enolates", Journal of the American Chemical Society, 1981, vol. 103, No. 8, pp. 2127-2129.
Malosh, Chrysa F., et al., "Catalytic Cross-Coupling of Alkylzinc Halides with α-Chloroketones", Journal of the American Chemical Society, 2004, vol. 126, No. 33, pp. 10240-10241.
Fischer, Christian, et al., "Asymmetric Nickel-Catalyzed Negishi Cross-Couplings of Secondary α-Bromo Amides with Organozinc Reagents", Journal of the American Chemical Society, 2005, vol. 127, No. 13, pp. 4594-4595.
Oppolzer, Wolfgang, et al., "Asymmetric alkylation of N-acylsultams: A general route to enantiomerically pure, crystalline C(α, α)-disubstituted carboxylic acid derivatives", Tetrahedron Letters, 1989, vol. 30, No. 41, pp. 5603-5606. (Abstract).
Cahiez, Gerard, et al., "Iron-Catalyzed Alkylations of Aromatic Grignard Reagents", Angewandte Chemie. 2007, vol. 119, No. 23, pp. 4442-4444. (Abstract).
Levene, P. A., et al. "The Configurational Relationships of Dialkylacetic Acids", Journal of Biological Chemistry, 1926, vol. 70, pp. 211-217.
Petit, Yves, et al., "Stereoselective Synthesis of Optically Active α-Methyl Esters", Tetrahedron Letters, 1990, vol. 31, No. 15, pp. 2149-2152.
Dragovich, Peter S., et al., "Structure-Based Design, Synthesis, and Biological Evaluation of Irreversible Human Rhinovirus 3C Protease Inhibitors. 8. Pharmacological Optimization of Orally Bioavailable 2-Pyridone—Containing Peptidomimetics", Journal of Medicinal Chemistry, 2003, vol. 46, No. 21, pp. 4572-4585.
Hatano, Manubu, et al., "Highly Efficient Alkylation to Ketones and Aldimines with Grignard Reagents Catalyzed by Zinc(II) Chloride", Journal of the American Chemical Society, 2006, vol. 128, No. 31, pp. 9998-9999.
Studte, Christopher, et al., "Zinc-Catalyzed Enantiospecific $sp^3$-$sp^3$ Cross-Coupling of α-Hydroxy Ester Triflates with Grignard Reagents", Angewandte Chemie International Edition, 2008, vol. 47, pp. 5451-5455.
Hanessian, S., et al., "Heteroatom-Assisted Substitution of Acyclic Secondary Tosylates with Lithium Dialkylcuprates: An Expedient Route to Stereochemically Defined Deoxypropionate and Related Biosynthetic Subunits", Journal of Organic Chemistry, 1989. vol. 54. No. 25, pp. 5831-5833.
International Search Report for PCT/EP2008/007818.
Written Opinion of the International Searching Authority for PCT/EP2008/007818.

*Primary Examiner* — Kamal Saeed
(74) *Attorney, Agent, or Firm* — Curatolo Sidoti Co., LPA; Joseph G. Curatolo; Salvatore A. Sidoti

(57) ABSTRACT

A method for the production of optically active α-alkylcarbonyl compounds with retention of the stereo information of the starting compound. The starting compound used here is a carbonyl compound which has, in the α-position, a leaving group which is substituted by an alkyl group with inversion of the configuration. The substitution of the leaving group is effected with the use of an alkylmagnesium Grignard and a zinc (II) salt or a zinc organyl. The method permits the production of optically active α-alkylcarbonyl compounds at very mild temperatures (for example 0° C.) with the use of starting compounds which are easy to prepare and economical and nontoxic catalysts, it also being possible to achieve a very high yield.

12 Claims, 3 Drawing Sheets

1  2  3  4

M = Li or MgX

METHOD FOR THE PRODUCTION OF OPTICALLY ACTIVE ALPHA ALKYL CARBONYL COMPOUNDS

CROSS REFERENCE TO RELATED APPLICATIONS

This application is a national stage application of International Application No. PCT/EP2008/007818, filed 18 Sep. 2008, which claims priority from German Patent Application Serial No. 10 2007 045 624.9, filed 24 Sep. 2007, from which applications priority is claimed, and which are incorporated herein by reference.

The present invention relates to a method for the production of optically active α-alkylcarbonyl compounds with retention of the stereo information of the starting compounds. Starting compounds used here are carbonyl compounds which have, in the α-position to the carbonyl group, a leaving group which is substituted by an alkyl, alkenyl or aryl group with inversion of the configuration. The substitution of the leaving group is effected with the use of an alkyl, alkenyl or arylmagnesium Grignard and of a zinc (II) salt or of a zinc organyl.

Optically active α-alkylcarbonyl compounds are important intermediates in the synthesis of numerous medical active substances. There is a multiplicity of different possibilities for their production. What is decisive here is that the production process permits a very high enantiomeric excess (ee) of the product so that it can be used for the active substance synthesis.

One possibility for the preparation of the optically active α-alkylcarbonyl compounds is the α-alkylation of chiral enolates (Evans et al., *Asymmetric synthesis*, 1984, Morrison J. D., Ed.: Academic Press, New York, Vol. 3, p. 1; Oppolzer et al., *Helv. Chim. Acta*, 1985, 68, 212). The oxazolidinone method developed by Evans et al. uses for this purpose an oxazolidinone as an auxiliary, with which the carbonyl compound which is to be alkylated is subjected to an addition reaction. An alkyl group is then added to this intermediate in the enolate form (cf. FIG. 1, and Evans et al., *J. Am. Chem. Soc.*, 1981, 103, 2127).

In the method of Oppolzer et al., a sultam is used as an auxiliary (cf. FIG. 2) and can be hydrolyzed after α-alkylation to give a chiral α-alkylcarboxylic acid (Oppolzer et al., *Tetrahedron Lett.*, 1989, 30, 5603).

Although the methods described above permit a high enantioselectivity, the chiral auxiliaries are not suitable for the synthesis on a large scale.

In particular, the chiral auxiliaries must often be optimized for the starting compound, with the result that such a method is particularly inconvenient. Other methods start from chiral α-chloroketones (Ready et al., *J. Am. Chem. Soc.*, 2004, 126, 10240) or racemic α-bromamides with the use of chiral ligands (Fu et al., *J. Am. Chem. Soc.*, 2005, 127, 4594). Considerable disadvantages likewise occur here since the methods are generally substrate-specific and/or require expensive and in some cases toxic catalysts. Furthermore, the desired enantiomeric purity often cannot be achieved or there is sometimes a complete loss of the stereo information, as in the case of the economical iron catalysts (Cahiez et al., *Angew. Chem.*, 2007, 119, 1).

Another approach to this synthesis is the resolution of racemates, which can be carried out, for example, with the use of a quinine salt (Levene et al., *J. Biol. Chem.*, 1926, 70, 211). Here, first 2-methylhexanoic acid is converted into the quinine salt and separated into the racemates by recrystallization. Although the method of racemate resolution is economical, the recrystallization results in greatly decreased yields.

A further method is ester hydrolysis using enzymes, for example esters of racemic 2-methylhexanoic acid being hydrolyzed with the use of lipases and esterases (Ozaki et al., *Chem. Abs.*, 1997, 127, 276440). However, these methods are likewise unsuitable for use on an industrial scale since the required enzymes are very expensive and, although some of the enzymes give a high enantiomeric excess, the reaction takes place slowly and permits only a low conversion rate.

The production of optically active α-alkylcarbonyl compounds can also be effected by asymmetrical hydrogenation. Particularly suitable here is the Ruthenium-BINAP complex (*Asymmetric Synthesis*, Morrison J. D., Ed.; Academic Press, 1985, Vol. 5). Although this method is suitable for a large industrial scale, it requires an, expensive and complicated technology and the catalysts are generally substrate-specific. In the case of 2-methylhexanoic acid, it gives in the end only an enantiomeric excess of 90%. Moreover, the asymmetrical hydrogenation also does not permit an economical production method.

Substantially simpler than the stereoselective synthesis is the access to enantiomerically pure α-hydroxyesters, which can be obtained from the chiral pool (naturally occurring and enantiomerically pure compounds) (FIG. 3). These include the naturally occurring α-chiral amino acids, which can be easily converted into the corresponding α-hydroxy acids with retention of the stereo information, with the result that the range of substrates is extended by a further very important class of substances (FIG. 4).

Larchevêque et al. were able to show that α-trifluorosulphoxy esters can be stereo selectively substituted with stoichiometrically used dialkyl cuprates. Owing to the competing elimination and reduction reactions, the yields achieved here with various Grignard reagents are, however, only 35-65% (FIG. 5). Moreover, the reaction procedure requires at least two equivalents of the alkylating reagent and a stoichiometric amount of copper salt and low temperatures down to −80° C. (Larchevêque et al., *Tet. Lett.*, 1990, 31, 2149).

An object of the present invention is therefore to provide a method for the production of chiral α-alkylcarbonyl compounds having a high enantiomeric excess, which can be carried out in a simple manner with the use of a catalytic amount of economical and nontoxic metal salt, and starting compounds which can be easily handled and can be simply prepared. A further object here is to find reaction conditions which make cooling to low temperature unnecessary.

These objects are achieved by the method according to the invention, as described in the claims. The present invention therefore relates to a method for the production of compounds of the formula I:

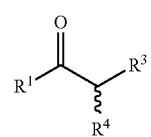

wherein a compound of the formula II

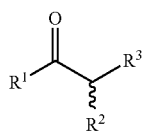

is reacted with $R^4MgX$ and $ZnY_2$ or $R^4MgX$ and $ZnR^4_2$, preferably with $R^4MgX$ and $ZnY_2$, with inversion of the stereoconfiguration at the α-carbonyl carbon atom, to give a compound according to formula I, in which $R^1$ may be OM, O—$R^5$ or $NR^5R^6$, where M maybe a metal ion, preferably sodium or potassium, and $R^5$ and $R^6$, independently of one another may be a straight-chain or branched alkyl radical, alkenyl radical, arylalkyl radical, aryl radical or heteroaryl radical, in which $R^2$ is a sulphonate leaving group, a phosphonate leaving group, a carboxylate leaving group, a carbamate leaving group, a carbonate leaving group or a halide.

in which $R^3$ is a straight-chain or branched alkyl radical, alkenyl radical, arylalkyl radical, aryl radical or heteroaryl radical which may have 5-8 carbon atoms and 1-2 hetero atoms, selected from O, N, P and S, as substituents or may be interrupted by the hetero atoms, in which $R^4$ represents a straight-chain or branched alkyl radical, alkenyl radical, arylalkyl radical, aryl radical or heteroaryl radical, in which, in the case of $R^1$ to $R^6$, an alkyl radical may have 1-15 carbon atoms, an alkenyl radical 2-15 carbon atoms, an arylalkyl radical 5-15 carbon atoms, an aryl radical 5-10 carbon atoms and a heteroaryl radical 5-8 carbon atoms and 1-2 hetero atoms, selected from O, N, P and S, in which X is a halogen, preferably chlorine, and in which Y may represent a sulphonate, a sulphate, a carboxylate, an alcoholate, a nitrate, a chalcogen or a halogen, preferably a halogen, more preferably chlorine.

More preferably, the method according to the invention is carried out at temperatures of more than −30° C.

Even more preferably, in the method according to the invention, the compounds of the formula II are used with an enantiomeric excess (ee) of more than 95% and the compounds of the formula I are prepared with an enantiomeric excess of more than 95%.

In a more preferred embodiment of the method according to the invention, 0.5-25% by weight of $ZnY_2$ or $ZnR^4_2$, based on the amount of the compound of the formula II, are used.

More preferably, tetrahydrofuran, 2-methyltetrahydrofuran or diethyl ether or a mixture of these solvents is used in the method according to the invention as a solvent for the reaction.

In a further preferred embodiment of the method according to the invention, the radicals $R^1$ to $R^6$ are characterized in that an alkyl radical comprises 1-10 carbon atoms, an alkenyl radical comprises 2-10 carbon atoms, an arylalkyl radical comprises 5-10 carbon atoms, an aryl radical comprises 5-8 carbon atoms and a heteroaryl radical comprises 5-7 carbon atoms and 1-2 hetero atoms, selected from O, N, P and S.

The radical $R^2$ is an alkanesulphonic acid group, a phosphate, carboxylic, carbamate or carbonate group or a halogen.

In a preferred embodiment of the method according to the invention, $R^2$ represents an alkane sulphonic acid group, more preferably a fluorinated alkanesulphonic acid group having 1-9 fluorine atoms, even more preferably a trifluoromethanesulphoxy group or a perfluorobutanesulphoxy group.

Even more preferably, $R^4$ represents a methyl, ethyl, isopropyl, n-butyl, isobutyl, sec-butyl, cyclohexyl, octyl, lauryl, allyl, methallyl, vinyl, phenyl, benzyl, 3-benzyloxypropyl and 3-benzyloxy-2-methylpropyl group.

In a more preferred embodiment of the method according to the invention, 1-2 equivalents $R^4MgX$, based on the amount of the compounds of the formula II, are used.

In an even more preferred embodiment of the method according to the invention, the compounds of the formula II are prepared from naturally occurring, chiral compounds.

In another preferred embodiment of the method according to the invention, the compounds of the formula II are prepared from the group consisting of: amino acids, L-lactic acid, L-malic acid, L-mandelic acid, L-tartaric acid.

The "wavy" representation of the C—C bond between $R^4$ and the α-carbon of the carbonyl compound and $R^2$ and the α-carbon of the carbonyl compound in the figures and the formulae I and II indicates that $R^4$ or $R^2$ may project either "forwards" or "backwards" relative to the plane of the paper. The method according to the invention leads to the inversion of the stereoconfiguration in the α-position to the carbonyl group so that $R^4$ in formula I "projects forwards" if $R^2$ in the starting compound according to formula II "projects backwards". In the other case, $R^4$ projects "backwards" if $R^2$ in the starting compound of the formula II projects forwards.

The method according to the invention permits production of α-alkylcarbonyl compounds at relatively high temperatures (for example 0° C.). Advantageously, the method according to the invention permits the use of economical, nontoxic, environmentally compatible $ZnCl_2$ in catalytic or very small amounts. By means of the method according to the invention and the use of the organometallic reagents which are easy to prepare, a very wide range of carbonyl compounds which have a leaving group in the α-position can be converted into α-alkylcarbonyl compounds in high yields.

Furthermore, the organometallic reagents required for the method according to the invention are easy to handle and economical and are already widely used in industry. The method according to the invention is therefore particularly suitable for production on a large scale. Advantageously, the optically active carbonyl compounds having a leaving group in the α-position can be synthesised easily, without chromatographic separation methods, from the economical, naturally occurring chiral compounds, which are also relatively stable and can be stored at low temperatures over a long period. The use of expensive chiral ligands or auxiliaries can be dispensed with.

By means of the reaction procedure at relatively high temperatures, an expensive low-temperature cooling technique can be dispensed with and the reactions can nevertheless be readily controlled—compared with reactions at room temperature—even in large reactors. Moreover, the recovery of the leaving group is possible in some cases, with the result that the production costs can be further reduced. Furthermore, the working-up and the isolation of the reaction products can be easily carried out with the use of fractional distillation.

In contrast to enolate chemistry, in which the alkyl radicals are introduced as electrophiles, the method according to the invention provides efficient and general access to optically active α-alkylcarbonyl compounds via the introduction of the alkyl radical as a nucleophile in excellent yields. Particularly through the access to enantiomerically pure α-alkylcarbonyl compounds having secondary radicals in the α-position (cf. examples), the method according to the invention has an advantage over chiral enolate chemistry, for which secondary electrophiles are unsuitable.

However, the stereoselective alkylation with nucleophiles, described by Fu et al. (Fu et al., *J. Am. Chem. Soc.,* 2005, 127, 4594), also provides an efficient and general method for the selective introduction of a secondary radical. On the other hand, in the method according to the invention, even β-branched carbonyl compounds having a leaving group in the α-position are suitable as substrates (cf. examples), with the result that vicinal stereocentres can be established.

A further advantage of the method according to the invention is the possibility of being able to use esters and carboxylates as well as amides as starting compounds.

The method according to the invention can be carried out with the use of the reaction conditions and reactants described below. Here, in the starting compound of the formula II and the product with the formula II, all preferred radicals $R^1$-$R^4$ can be combined with all other preferred radicals $R^1$-$R^4$.

The reaction scheme of the method according to the invention is shown in FIG. 6. Starting compounds which may be used here are compounds of the general formula II. The compounds of the formula II have a chiral centre in the α-position to the carbonyl group. The reaction mechanism of the method according to the invention is formally an SN2 reaction, the leaving group which is present in the α-position to the carbonyl group being nucleophilically substituted with inversion of the stereoconfiguration. Consequently, the method according to the invention takes place with retention of the stereo information.

Here, the expression "retention of the stereo information" means that one enantiomer of the compound of the formula II is converted into exactly one enantiomer of the α-alkylcarbonyl compound of the formula I with inversion of the stereoconfiguration. Consequently, the enantiomeric purity or the enantiomeric excess of the α-alkylcarbonyl compound produced corresponds to the enantiomeric purity of the starting compound used.

The expression "inversion of the stereoconfiguration" in the α-position to the carbonyl group means that, in the case of substitution of $R^2$ by $R^4$, an inversion of the configuration at the carbon atom in the α-position to the carbonyl group takes place so that $R^4$ "projects forwards" relative to the plane of the paper if $R^2$ in the starting compound of the formula II "projects backwards", $R^4$ "projects backwards" if $R^2$ in the starting compound of the formula II "projects forwards".

Preferably, the compounds of the formula II having an enantiomeric excess of 95% ee, more preferably >96% ee, even more preferably >97% ee, even more preferably >98% ee and most preferably >99% ee are used.

For the method according to the invention, all starting compounds according to formula II are suitable. Methods for the production of these chiral compounds are known to the person skilled in the art. The compounds of formula II are also preferably produced from naturally occurring chiral compounds. Naturally occurring chiral acids, such as, for example, amino acids or L-lactic acid, are particularly preferred. With the use of amino acids, the α-hydroxy acid is first prepared according to the method shown in FIG. 4 and described above. Said α-hydroxy acid can then be esterified, as, for example, also L-lactic acid or the other acids from FIG. III. The hydroxyl group in the α-position is then converted into a leaving group in order to obtain a compound of the general formula II.

Methods for the production of compounds of the generally formula II are known to the person skilled in the art. Thus, a multiplicity of α-hydroxy acids, esters and amides are commercially available, for example tert-butyl D-lactic acid (Fluka), or can be prepared by means of the corresponding technical literature, for example via esterification methods (*Esterification,* Otera Junzo, Wiley-VCH, Weinheim, 2003, p. 1). Methods for converting the hydroxyl function into a leaving group are likewise known, for example into a trifluoromethanesulphoxy ester (Dragovich et al. *J. Med. Chem.,* 2003, 46, 4572), these also being commercially available in some cases, as, for example, the triflate of ethyl L-lactate (Fluka, Aldrich).

Carbonyl compounds which are known as "chiral pool" and are naturally occurring compounds are particularly preferred as starting compounds with the production of compounds of the formula II. Particularly preferred compounds here for the production of compounds of the formula II are: amino acids, L-lactic acid, L-mandelic acid, L-malic acid, L-tartaric acid. These compounds are converted into the starting compounds of the general formula II by esterification and introduction of a leaving group in the α-position of the carbonyl compound (α-*Hydroxy Acids in Enantioselective Synthesis,* 1997, Coppola G. M., Schuster H. F., VCH, Weinheim, p. 1).

The compounds of the general formula II have the radicals $R^1$ (with the radicals $R^5$ and $R^6$), $R^2$ and $R^3$.

Here, $R^1$ together with the carbonyl compound can give a carboxylic, an ester or an amide. Preferably, $R^1$ is OM, O—$R^5$ or NR$^5$R$^6$, where M can represent a metal ion, preferably sodium or potassium, and $R^5$ and $R^6$, independently of one another, can represent a straight-chain or branched alkyl radical, alkenyl radical, arylalkyl radical, aryl radical or heteroaryl radical. Here, an alkyl radical preferably has 1-15 carbon atoms, an alkenyl radical 2-15 carbon atoms, an arylalkyl radical 5-15 carbon atoms, an aryl radical 5-10 carbon atoms and a heteroaryl radical 5-8 carbon atoms and 1-2 hetero atoms, selected from O, N, P and S. More preferably, an alkyl radical has 1-10, more preferably 1-7, carbon atoms, an alkenyl radical 2-10, more preferably 2-7, carbon atoms, an arylalkyl radical 5-10, more preferably 5-8, carbon atoms, an aryl radical 5-8, more preferably 5-6, carbon atoms and a heteroaryl radical 5-7, more preferably 5-6, carbon atoms and 1-2 hetero atoms, selected from O, N, P and S, more preferably selected from O, N and S. More preferably, $R^1$ is O—$R^5$. Even more preferably, $R^5$ here is methyl, ethyl, isopropyl, isobutyl, benzyl or tert-butyl, more preferably tert-butyl.

$R^2$ represents a leaving group, preferably selected from the group consisting of: sulphonate groups, phosphate groups, carboxylate groups, carbamate groups, carbonate groups and halides. The expression "sulphonate groups" refers to all groups derived from sulphonic acid. Here, alkanesulphonic acid groups are preferred and halogenated alkanesulphonic acid groups having 1-9 halogen substituents, more preferably having 1-9 fluorine atoms, are more preferred. Perfluorinated alkanesulphonic acid groups are even more preferred and the trifluoromethanesulphonic acid group (triflate) and perfluorobutanesulphonic acid group (nonaflate) are most preferred. The expression "phosphate groups" refers to all groups derived from phosphoric acid. Alkyl and aryl phosphate groups are preferred here and halogenated alkyl and aryl phosphate groups having 1-14 halogen substituents, more preferably having 1-14 fluorine atoms, are more preferred. Perfluorinated alkyl and aryl phosphate groups are even more preferred. The expression "carboxylate groups" refers to all groups derived from carboxylic acid. Alkyl and aryl carboxylate groups are preferred here and halogenated alkyl and aryl carboxylate groups having 1-10 halogen substituents, more preferably 1-10 fluorine atoms, are more preferred. Perfluorinated alkyl and aryl carboxylate groups are even more preferred. The expression "carbamate group" refers to all groups derived from carbamic acid. Alkyl and aryl carbamate groups are preferred here and halogenated alkyl and aryl carbamate groups having 1-14 halogen substituents, more preferably having 1-14 halogen substituents, more preferably having 1-14 fluorine atoms, are more preferred. Perfluorinated alkyl and aryl carbamate groups are even more preferred. The expression "carbonate group" refers to all groups derived from carbonic acid. Alkyl and aryl carbonate groups are preferred here and halogenated alkyl and aryl carbonate groups having 1-10 halogen substituents, more preferably 1-10 fluorine atoms, are more preferred. Perfluorinated alkyl and aryl carbonate groups are even more preferred. The preferred halide leaving group is chloride.

Preferably, $R^3$ represents a straight-chain or branched alkyl radical, alkenyl radical, arylalkyl radical or aryl radical which may have 1-7, more preferably 1-5, even more preferably 1-3, hetero atoms, selected from O, N and S as substituents, or may be interrupted by the hetero atoms. The expression that an alkyl radical, alkenyl radical, arylalkyl radical or aryl radical "can be interrupted" by hetero atoms means that the hetero atoms may be present between the carbon atoms and the alkyl chain and in the aryl ring. If hetero atoms are present as substituents, they can preferably also carry protective groups, for example if they are hydroxyl or amino groups, in order to avoid secondary reactions with the organometallic compound.

Preferably, with respect to $R^3$, an alkyl radical has 1-5 carbon atoms, an alkenyl radical 2-15 carbon atoms, an arylalkyl radical 5-15 carbon atoms, an aryl radical 5-10 carbon atoms and an heteroaryl radical 5-8 carbon atoms and 1-2 hetero atoms, selected from O, N, P and S. More preferably, an alkyl radical has 1-10, more preferably 1-7, carbon atoms, an alkenyl radical 2-10, more preferably 2-7, carbon atoms, an arylalkyl radical 5-10, more preferably 5-8, carbon atoms, an aryl radical 5-8, more preferably 5-6, carbon atoms and a heteroaryl radical 5-7, more preferably 5-6, carbon atoms and 1-2 hetero atoms, selected from O, N, P and S, more preferably selected from O, N and S. More preferably, $R^1$ is O—$R^5$. Even more preferably, $R^5$ here is methyl, ethyl, isopropyl, isobutyl, benzyl or tert-butyl, more preferably tert-butyl.

In order to substitute the leaving group in the α-position of the carbonyl group, a "nucleophilic alkyl group" can be produced with the use of a magnesium Grignard reagent and $ZnY_2$. Here, it is postulated that the active species is based on a trialkyl zincate (II) complex or a trialkenyl zincate (II) complex or a triaryl zincate (II) complex, $R^4_3ZnMgX$. $R^4_3ZnMgX$ forms from $R^4MgX$ and $R^4_2Zn$, which is first formed from $ZnY_2$ and $R^4MgX$ (Ishihara et al., *J. Am. Chem. Soc.* 2006, 128, 9998). For the method according to the invention, any magnesium Grignard reagents are suitable. Magnesium Grignard reagents of the general formula $R^4MgX$, in which X preferably represents a halogen, more preferably chlorine, bromine or iodine, even more preferably chlorine, are particularly preferred. For the method according to the invention, any zinc salts are suitable. Particularly preferred zinc salts are those of the general formula $ZnY_2$, in which Y preferably represents a sulphonate, a sulphate, a carboxylate, an alcoholate, a nitrate, a chalcogen or a halogen, more preferably chlorine, bromine, iodine, even more preferably chlorine. Furthermore, it is also possible to use the zinc organyl $ZnR^4_2$ directly instead of $ZnY_2$, since the active species $R^4_3ZnMgX$ forms from $ZnR^4_2$ and $R^4MgX$, as described above.

$R^4$ preferably represents a straight-chain or branched alkyl radical, alkenyl radical, arylalkyl radical, aryl radical or heteroaryl radical. Preferably, an alkylradical has 1-15 carbon atoms, an alkenyl radical 2-15 carbon atoms, an arylalkyl radical 5-15 carbon atoms, an aryl radical 5-10 carbon atoms and a heteroaryl radical 5-8 carbon atoms and 1-2 hetero atoms, selected from O, N, P and S. More preferably, an alkyl radical has 1-10, more preferably 1-7, carbon atoms, an alkenyl radical 2-10, more preferably 2-7, carbon atoms, an arylalkyl radical 5-10, more preferably 5-8, carbon atoms, an aryl radical 5-8, more preferably 5-6, carbon atoms and a heteroaryl radical 5-7, more preferably 5-6, carbon atoms and 1-2 hetero atoms, selected from O, N, P and S. Particularly preferably $R^4$ represents a methyl, ethyl, isopropyl, n-butyl, isobutyl, sec-butyl, cyclohexyl, octyl, lauryl, allyl, methallyl, vinyl, phenyl, benzyl, 3-benzyloxypropyl and 3-benzyloxy-2-methylpropyl group.

The magnesium Grignard reagent is preferably used in amounts of from 1 to 2, more preferably 1.2-1.6, equivalents (eq.), based on the amount of the starting compound of the formula II.

In order to produce the desired organometallic reagent, $ZnY_2$ is used in dry form. 0.5-25% by weight of $ZnY_2$, based on the amount of starting material of the formula II, are preferably used here. The $ZnY_2$ can also be complexed here by solvent molecules, for example TMEDA (tetramethylethylenediamine). $Zn(OA_c)_2$ and $ZnCl_2TMEDA$ at 0° C. and $Zn(OTf)_2$ at −20° C. have also proved to be suitable zinc catalysts.

Solvents which are suitable for Grignard reactions are also preferably used for the method according to the invention. These solvents are known to the person skilled in the art. Tetrahydrofuran, 2-methyltetrahydrofuran, diethyl ether or mixtures of these two solvents are preferably used. Owing to the hydrolysis of organometallic compounds by water, an organic solvent which is as anhydrous as possible should be used.

The method according to the invention is preferably carried out at temperatures between −30° C. and 30° C., more preferably between −15° C. and 10° C., more preferably between −10° C. and 10° C., even more preferably between −5° C. and 5° C. and most preferably at 0° C. The duration of reaction is preferably from 10 minutes to 3 hours, even more preferably from 1 hour to 2 hours. The exact end of the reaction can optionally be determined by customary methods. Suitable methods here are methods of measurement such as GC-MS (gas chromatography combined with mass spectrometry) or NMR (Nuclear Magnetic Resonance) spectroscopy.

The procedure for the method according to the invention is described further in the examples and comprises a first step in which the dry zinc (II) salt $ZnY_2$ is dissolved in dry solvent and then cooled (for example to 0° C.). The solvent can also be cooled before the addition of the zinc (II) salt $ZnY_2$. Thereafter, the starting material of the formula II and subsequently the Grignard reagent can be added or the order of addition can be reversed. The purification of the reaction mixture can be effected by customary methods, for example by distillation. The characterization of the products can be effected by customary methods, for example with the use of GC-MS or NMR spectroscopy.

DESCRIPTION OF THE FIGURES

Abbreviations Used:
n-BuLi=n-butyllithium; THF=tetrahydrofuran; NaHMDS=sodium hexamethyldisilazide; MeI=methyl iodide; KOH=potassium hydroxide; NaH=sodium hydride; HMPA=hexamethylphosphoramide and LiOH=lithium hydroxide; Tf=triflate.

EXAMPLE 1

Figure 1:
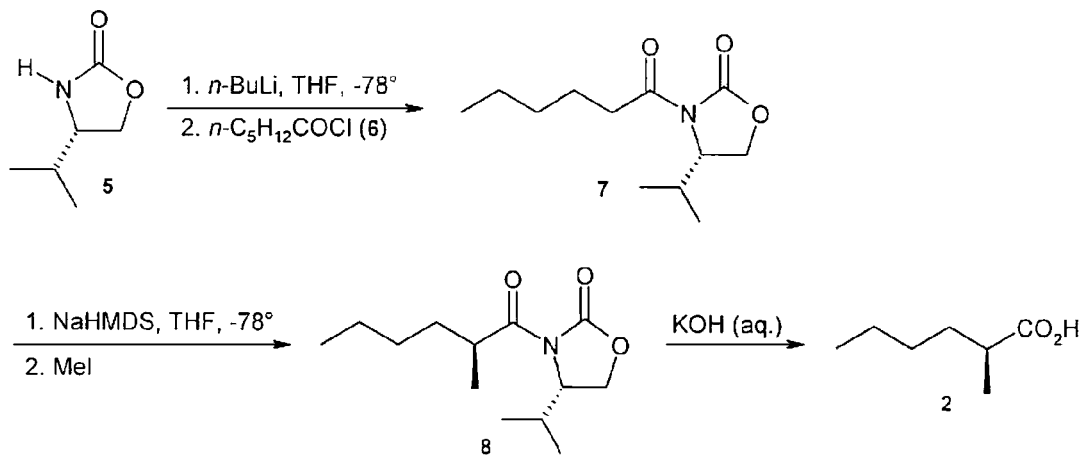
FIG. 1 shows the oxazolidinone method for the production of α-alkylcarbonyl compounds. Here, an acylation reaction of the starting compound 5 is effected with the use of n-BuLi and n-$C_5H_{12}$COCl. The compound 7 formed thereby can be subjected in the enolate form to an addition reaction with a methyl group, and the α-alkylcarbonyl compound can then be obtained in aqueous alkaline solution.
Figure 2:
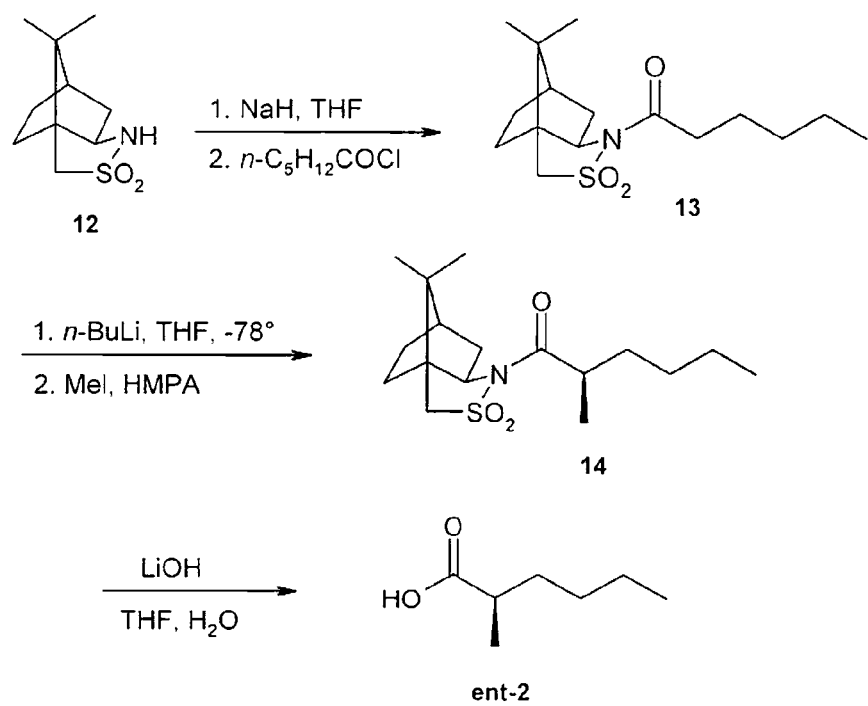
FIG. 2 shows the Oppolzer sultam method for the production of α-alkylcarbonyl compounds. Here, the Oppolzer sultam (compound 12) is used as a chiral auxiliary agent and, after an addition reaction of a carbonyl compound with the chiral auxiliary reagent, a stereoselective addition of a methyl group in the α-position of the carbonyl compound can be effected and, with the use of lithium-hydroxide, the free α-alkylcarbonyl compound can then be obtained.
Figure 3:
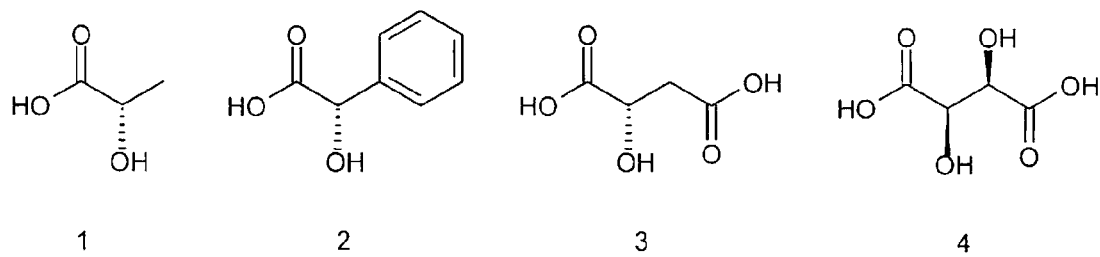
FIG. 3 shows naturally occurring enantiomerically pure α-hydroxy acids (chiral pool) which can be used for the production of the starting compounds according to formula II. Compound 1=L-lactic acid; compound 2= mandelic acid; compound 3=L-malic acid; compound 4=L-tartaric acid.
Figure 4:
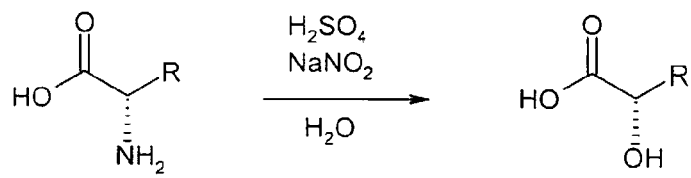
FIG. 4 shows the production of α-hydroxy acids from chiral amino acids with the use of sulphuric acid and sodium nitrite.
Figure 5:
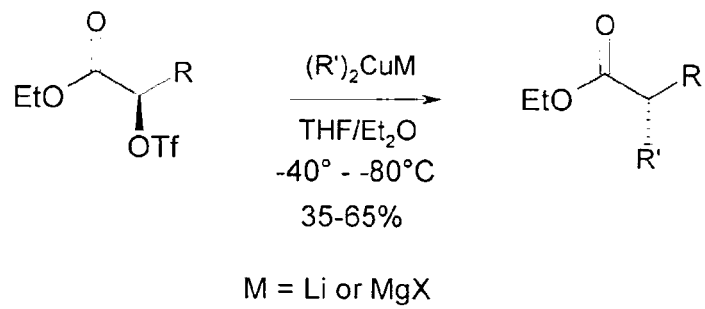
FIG. 5 shows the stereoselective reaction of α-trifluoromethanesulphoxy esters according to Larchevêque et al., with dialkyl cuprates at low temperatures and with the use of a stoichiometric amount of copper salt.
Figure 6:
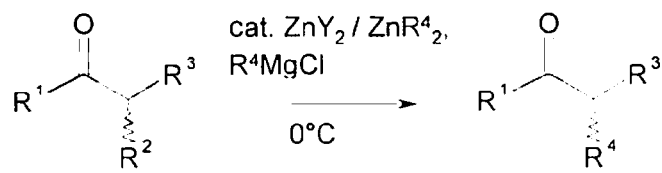
FIG. 6 shows the method according to the invention using $ZnY_2$ and $R^4MgCl$ at 0° C.

Production of Optically Active Tert-Butyl (S)-2-Trifluoromethanesulphonyloxypropionate In a 500 ml round-bottomed flask, 3.00 g of tert-butyl L-lactate (ee>99%) was dissolved in 165 ml of absolute dichloromethane and cooled to 0° C. under argon. Thereafter, first 3.10 ml of 2.6-lutidine and then slowly 4.15 ml of trifluoromethanesulphonic anhydride were added in succession and the reaction was stirred for 50 min at 0° C. Thereafter, the reaction mixture was diluted with 400 ml of petroleum ether, washed 4 times with 250 ml of a 3:1 mixture of saturated aqueous sodium chloride solution and 1 N hydrochloric acid, dried over $MgSO_4$ and concentrated in vacuo. The residue was applied to a silica gel filter and washed off said filter with a 1:1 mixture of petroleum ether and dichloromethane. After removal of the solvent, the pure tert-butyl (S)-2-trifluoromethanesulphonyloxypropionate (ee>99%) was obtained in a yield of 90%.

EXAMPLE 2

Production of Optically Active Tert-Butyl (S)-2-Methylhexanoate

In a 10 ml Schlenk tube, 3.5 mg of dry zinc chloride was dissolved in 3.0 ml of absolute tetrahydrofuran and cooled to 0° C. under argon. Thereafter, 279 mg of tert-butyl (S)-2-trifluoromethanesulphonyloxypropionate (ee>99%) and 0.700 ml of n-butylmagnesium chloride (2.00 M solution in THF) were added in succession and the reaction was stirred for 3 h at 0° C. Thereafter, the reaction mixture was diluted with petroleum ether, first water and then saturated ammonium chloride solution were added and the organic phase was separated off. This was applied directly to a silica gel filter and washed with petroleum ether. The product was then washed off with a petroleum ether/diethyl ether mixture (10:1) from the filter and freed from the solvent. The pure tert-butyl (S)-2-methylhexanoate (entry 3 in table 1)(ee>99%) was obtained in quantitative yield.

EXAMPLE 3

Production of Optically Active Tert-Butyl (2S)-2,3-Dimethylbutanoate

Tert-butyl trifluoromethanesulphonyloxypropionate was produced as in example 1. In a 10 ml Schlenk tube, 7.0 g of dry zinc chloride was dissolved in 3.0 ml of absolute tetrahydrofuran and cooled to 0° C. under argon. Thereafter. 279 mg of tert-butyl (S)-2-trifluoromethanesulphonyloxypropionate (ee>99%) and 0.820 ml of isopropylmagnesium chloride (1.70 M solution in THF) were added in succession and the reaction was stirred for 3 h at 0° C. Thereafter, the reaction mixture was diluted with petroleum ether, first water and then saturated ammonium chloride solution were added and the organic phase was separated off. This was applied directly to a silica gel filter and washed with petroleum ether. The products were then washed off with a petroleum ether/diethyl ether mixture (10:1) from the filter and freed from the solvent. 98 mol % of tert-butyl (2S)-2,3-dimethylbutanoate (entry 2 in table 1) (ee>99%) and 2 mol % of tert-butyl propionate were obtained. The target compound could be purified by means of a Kugelrohr distillation.

Both in example 2 and in example 3, the products can be directly isolated without problems by means of fractional distillation in a synthesis on a relatively large scale.

EXAMPLE 4

Summary of all Examples with Tert-Butyl Esters as Starting Compounds

Figure 7:
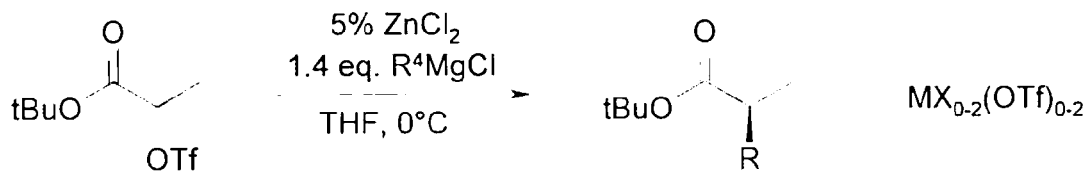
FIG. 7 shows the method according to the invention using a trifluorosulphonic acid group as a leaving group and the use of 5% of $ZnCl_2$ and 1.4 equivalents (eq.) of $R^4MgCl$ in THF at 0° C.

The α-alkylcarbonyl compounds listed in table 1 below were produced analogously to examples 1 and 2 (see also FIG. 7).

EXAMPLE 1

| Entry | R | Yield$^a$ | ee (%) |
|---|---|---|---|
| 1 | Et | quantitative | >99 |
| 2 | iPr | 98 | >99 |
| 3 | nBu | quantitative | >99 |
| 4 | iBu | quantitative$^b$ | >99 |
| 5 | sBu | 96 | >99 |
| 6 | Cy | 90$^c$ | >99 |
| 7 | Oct | quantitative | >99 |
| 8 | Lauryl | quantitative | >99 |
| 9 | Bn | quantitative | >99 |
| 10 | ⋀⋁OtBu | 94 | >99 |

-continued

| Entry | R | Yield[a] | ee (%) |
|---|---|---|---|
| 11 | /\/= | quantitative | >99 |

[a]Isolated yield,
[b]20% ZnCl$_2$,
[c]10% ZnCl$_2$

Abbreviations in the table: Et = Ethyl, iPr = isopropyl, nBu = n-butyl, iBu = isobutyl, sBu = sec-butyl, Cy = Cyclohexyl, Oct = Octyl, Bn = Benzyl Table 1 shows that both straight-chain and branched as well as aromatic Grignard reagents are suitable for the synthesis of optically pure α-alkylcarbonyl compounds. Particularly advantageous here is the possibility of being able to prepare enantiomerically pure α-alkylcarbonyl compounds having secondary alkyl radicals in the α-position.

EXAMPLE 5

Summary of the Examples with the Use of Different Tert-Butyl Esters

Figure 8:
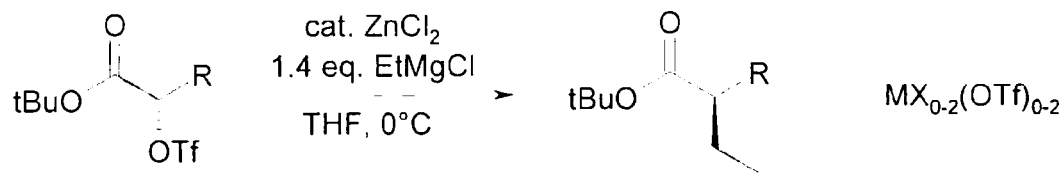
FIG. 8 shows the use of tert-butyl esters with triflate leaving groups in the α-position to the carbonyl group. These compounds are converted into the α-alkyl ester with the use of EtMgCl and $ZnCl_2$ at 0° C.

With the method according to the invention, a very wide range of carbonyl compounds having leaving groups can be used as starting compounds for the synthesis of α-alkylcarbonyl compounds. This is shown by the starting compounds of the general formula II which are presented in table 2. The associated reaction scheme is shown in FIG. 8. The syntheses were carried out according to the method from example 2.

TABLE 2

| Entry | Substrate | ZnCl$_2$ (mol-%) | Yield (%) |
|---|---|---|---|
| 1 | tBuO-C(O)-CH(OTf)-CH$_2$CH$_2$CH$_2$CH$_3$ | 5 | quantitative |
| 2 | tBuO-C(O)-CH(OTf)-CH(CH$_3$)$_2$ | 15 | quantitative |
| 3 | tBuO-C(O)-CH(OTf)-CH$_2$CH(CH$_3$)$_2$ | 10 | quantitative |
| 4 | tBuO-C(O)-CH(OTf)-CH(CH$_3$)CH$_2$CH$_3$ | 20 | quantitative |
| 5 | tBuO-C(O)-CH(OTf)-CH$_2$-Ph | 5 | quantitative |
| 6 | tBuO-C(O)-CH(OTf)-CH$_2$-OBn | 20 | quantitative |
| 7 | tBuO-C(O)-CH(OTf)-CH$_2$-C(O)-OtBu | 5 | quantitative |

The starting compounds shown in table 2 can all easily be synthesized from naturally occurring enantiomerically pure compounds (amino acids, entries 1-6; malic acid, entry 7). Even β-branched α-alkylcarbonyl compounds are suitable as starting compounds, with the result that the method according to the invention provides access to an unlimited number of optically active α-alkylcarbonyl compounds.

EXAMPLE 6

Use of α-Trifluorosulphoxyamides as Starting Compounds

Figure 9:
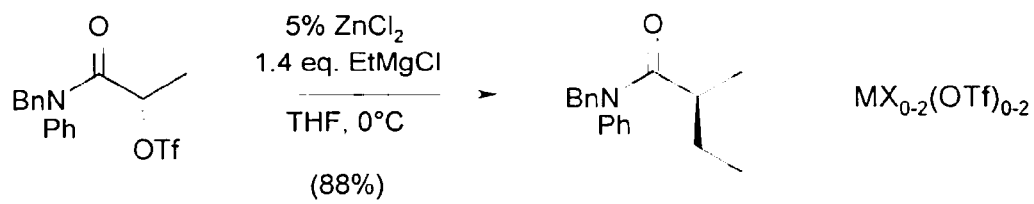
FIG. 9 shows the use of a benzylphenylamide with a triflate leaving group in the α-position to the carbonyl compound. This starting compound is converted into the corresponding α-alkylamide with EtMgCl and $ZnCl_2$.

FIG. 9 shows the use of α-trifluoromethanesulphoxyamides as starting compounds, which can be produced from the corresponding α-hydroxyamides by the method described in example 1. The synthesis of the chiral α-alkylamide was effected with the use of the method described in example 2. In the reaction shown in FIG. 9, it was possible to achieve a yield of 88%.

EXAMPLE 7

Production and Reaction of Further Amide Compounds

The reaction was effected as in examples 1 and 2 (cf. FIG. 9).

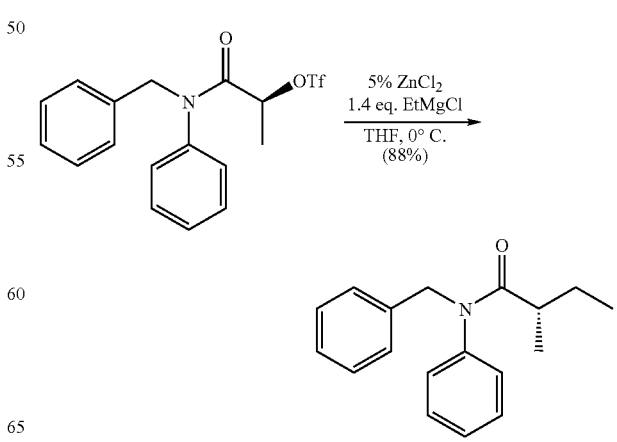

EXAMPLE 8

Production and Reaction of Ester Compounds Having a Nonaflate Leaving Group

EXAMPLE 8a

Production of Optically Active Tert-Butyl (S)-2-(Nonafluorobutane-1-Sulphonyloxy)Propionate

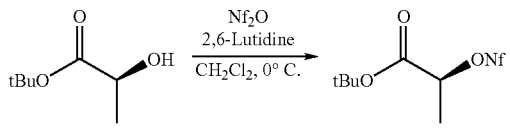

The production of tert-butyl nonafluorobutanesulphonyloxypropionate was effected with nonafluorobutanesulphonic anhydride as in example 1 with a yield of 82% (ee>99%).

EXAMPLE 8b

Production of Optically Active Tert-Butyl (S)-2-Methylhexanoate

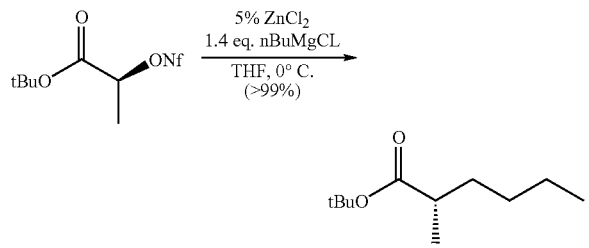

The production of tert-butyl (S)-2-methylhexanoate with tert-butyl (S)-2-(nonafluorobutane-1-sulphonyloxy)propionate was effected as in example 2 with a quantitative yield (ee>99%).

EXAMPLE 9

Carboxylate Compounds were Produced and Reacted as Follows

Production of the triflate of lactic acid:

EXAMPLE 9a

Production of Optically Active (S)-2-Trifluoromethanesulphonyloxypropionic acid

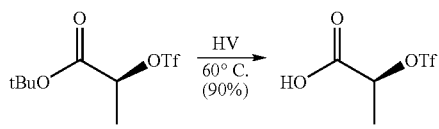

In a 10 ml round-bottomed flask, 1.00 g of tert-butyl (S)-2-trifluoromethanesulphonyloxypropionate (ee>99%) was heated under a high vacuum (0.01 mbar) at 60° C. The slightly yellowish residue contained pure (S)-2-trifluoromethanesulphonyloxypropionic acid (ee 99%) in a yield of 90%.

EXAMPLE 9b

Production of Optically Active (S)-2-Methylhexanoic Acid

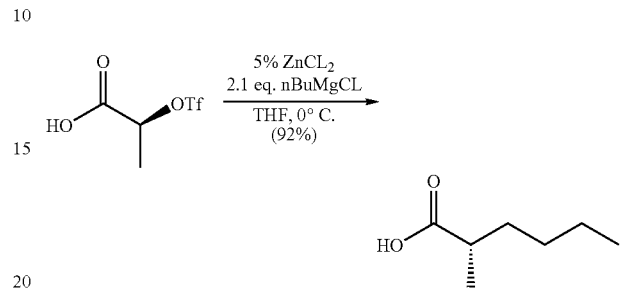

In a 10 ml Schlenk tube, 5.0 mg of dry zinc chloride was dissolved in 3.0 ml of absolute tetrahydrofuran and cooled to 0° C. under argon. Thereafter, 222 mg of (S)-2-trifluoromethanesulfonyloxypropionic acid (ee 99%) and 1.05 ml of n-butylmagnesium chloride (2.00 M solution in THF) were added in succession and the reaction was stirred for 3 h at 0° C. Thereafter, the reaction mixture was diluted with petroleum ether, saturated sodium carbonate solution was added and the organic phase was separated off. The aqueous phase was acidified with an aqueous 2 M HCl solution, saturated with NaCl and extracted 3 times with 10 ml of diethyl ether. The combined organic phases were dried over $MgSO_4$ and concentrated in vacuo. Pure (S)-2-methylhexanoic acid (ee 99%) was obtained in 92% yield.

As in example 8, in example 10 too, the products in the synthesis on a relatively large scale can be directly isolated without problems by means of a fractional distillation.

The invention claimed is:

1. A method for the production of compounds of the formula I:

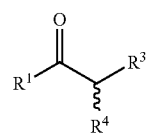

wherein a compound of the formula II,

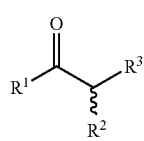

is reacted with $R^4MgX$ and $ZnY_2$ or $R^4MgX$ and $ZnR^4_2$, with inversion of the stereoconfiguration at the α-carbonyl carbon atom, to give a compound according to formula I, in which $R^1$ is OM, O—$R^5$ or $NR^5R^6$, where M is a metal ion and $R^5$ and $R^6$, independently of one another, represent a straight-chain or branched alkyl radical, alkenyl radical, arylalkyl radical, aryl radical or heteroaryl radical, in which $R^2$ is a sulphonate leaving group, phosphate leaving group, carboxylate leaving group, carbamate leaving group, carbonate leaving group or a halide, in which $R^3$ represents a straight-chain or branched alkyl radical, alkenyl radical, arylalkyl radical, aryl radical or heteroaryl radical which optionally has 5-7 carbon atoms and 1-2 hetero atoms, selected from O, N, P and S, as substituents or are interrupted by the hetero atoms, in which $R^4$ represents a straight-chain or branched alkyl radical, alkenyl radical, arylalkyl radical, arylradical or heteroaryl radical, in which, in $R^1$ to $R^6$, an alkyl radical has 1-15 carbon atoms, an alkenyl radical 2-15 carbon atoms, an arylalkyl radical 5-15 carbon atoms, an aryl radical 5-10 carbon atoms and a heteroaryl radical 5-8 carbon atoms and 1-2 hetero atoms, selected from O, N, P and S, in which X represents a halogen and in which Y represents a sulphonate, a sulphate, a carboxylate, an alcoholate, a nitrate, a chalcogen or a halogen.

2. The method according to claim 1, wherein the method is carried out at temperatures of more than −30° C.

3. The method according to claim 1, wherein the compounds of the formula II are used with an enantiomeric excess (ee) of more than 95% and the compounds of the formula I are prepared with an enantiomeric excess of more than 95%.

4. The method according to claim 1, wherein 0.5-25% by weight of $ZnY_2$ or $ZnR^4{}_2$, based on the amount of the compound of the formula II, are used.

5. The method according to claim 1, wherein tetrahydrofuran, 2-methyltetrahydrofuran or diethyl ether or a mixture of these solvents is used as a solvent for a reaction.

6. The method according to claim 1, wherein in $R^1$ to $R^6$ an alkyl radical comprises 1-10 carbon atoms, an alkenyl radical comprises 2-10 carbon atoms, an arylalkyl radical comprises 5-10 carbon atoms, an aryl radical comprises 5-8 carbon atoms and a heteroaryl radical comprises 5-7 carbon atoms and 1-2 hetero atoms, selected from O, N, P and S.

7. The method according to claim 1, wherein $R^2$ represents an alkanesulphonic acid group, phosphate group, carboxylate group, carbamate group, carbonate group or halogen.

8. The method according to claim 7, wherein $R^2$ is a triflate or nonaflate leaving group.

9. The method according to claim 1, wherein $R^4$ represents a methyl, ethyl, isopropyl, n-butyl, isobutyl, sec-butyl, cyclohexyl, octyl, lauryl, allyl, methallyl, vinyl, phenyl, benzyl, 3-benzyloxypropyl and 3-benzyloxy-2-methylpropyl group.

10. The method according to claim 1, wherein 1-2 equivalents of $R^4MgX$, based on the amount of the compound in the formula II, are used.

11. The method according to claim 1, wherein the compounds of the formula II are produced from naturally occurring, chiral compounds.

12. The method according to claim 1, wherein the compounds of the formula II are produced from compounds selected from the group consisting of: amino acids, L-lactic acid, L-malic acid, L-tartaric acid, and L-mandelic acid.

* * * * *